United States Patent
Knighton et al.

(10) Patent No.: US 7,625,489 B2
(45) Date of Patent: Dec. 1, 2009

(54) METHODS OF TREATING WATER USING DEVICES FOR WATER TREATMENT

(75) Inventors: David R. Knighton, Minneapolis, MN (US); Vance D. Fiegel, New Brighton, MN (US)

(73) Assignee: Embro Corporation, St. Louis Park, MN (US)

( * ) Notice: Subject to any disclaimer, the term of this patent is extended or adjusted under 35 U.S.C. 154(b) by 0 days.

(21) Appl. No.: 12/356,244

(22) Filed: Jan. 20, 2009

(65) Prior Publication Data

US 2009/0120871 A1    May 14, 2009

Related U.S. Application Data

(62) Division of application No. 11/106,049, filed on Apr. 14, 2005, now Pat. No. 7,497,947.

(60) Provisional application No. 60/562,196, filed on Apr. 14, 2004.

(51) Int. Cl.
*C02F 3/32* (2006.01)
(52) U.S. Cl. .................................... 210/602
(58) Field of Classification Search .............. 210/602, 210/767
See application file for complete search history.

(56) References Cited

U.S. PATENT DOCUMENTS

| | | |
|---|---|---|
| 221,909 A | 3/1879 | Collins |
| 239,564 A | 3/1881 | Smith |
| 413,621 A | 8/1889 | Glaister |
| 1,914,824 A | 6/1933 | Eberhard |
| 2,605,589 A | 8/1952 | Kuestner |
| 2,785,106 A | 3/1957 | Mendelsohn |
| 2,876,588 A | 3/1959 | Tietz et al. |
| 3,635,816 A | 1/1972 | Golub |
| 3,835,042 A | 9/1974 | Lalancette et al. |
| 3,890,910 A | 6/1975 | Angruner |
| 3,894,355 A | 7/1975 | Carothers |
| 3,903,267 A | 9/1975 | Miler et al. |
| 3,914,901 A | 10/1975 | Muldner |
| 3,961,444 A | 6/1976 | Skaife |
| 4,002,566 A | 1/1977 | Smith |
| 4,014,676 A | 3/1977 | Carter et al. |
| 4,079,543 A | 3/1978 | Stoller |
| 4,123,359 A | 10/1978 | Smith |
| 4,146,646 A | 3/1979 | Percival et al. |
| 4,190,981 A | 3/1980 | Muldner |
| 4,215,692 A | 8/1980 | Levesque |
| 4,272,527 A | 6/1981 | Belkevich et al. |
| 4,272,962 A | 6/1981 | Viscovich et al. |
| 4,402,941 A | 9/1983 | Vaillancourt |

(Continued)

FOREIGN PATENT DOCUMENTS

GB    2 134 791 A    8/1984

(Continued)

OTHER PUBLICATIONS

Asakawa, "Biologically Active Substances Obtained From Bryophytes[1,2]", *Journ. Hattori Bot. Lab. No.*, 50:123-142 (Sep. 1981).

(Continued)

*Primary Examiner*—Fred Prince
(74) *Attorney, Agent, or Firm*—Popovich, Wiles & O'Connell, P.A.

(57) ABSTRACT

A device for use in water comprising a carrier having an interior cavity and one or more openings allowing ingress to and egress from the interior cavity; and a moss contained within the interior cavity in which the carrier completely encloses the moss.

57 Claims, 4 Drawing Sheets

U.S. PATENT DOCUMENTS

| | | |
|---|---|---|
| 4,528,774 A | 7/1985 | Skaife |
| 4,537,590 A | 8/1985 | Pieniak |
| 4,551,165 A | 11/1985 | Warner |
| 4,560,372 A | 12/1985 | Pieniak |
| 4,588,400 A | 5/1986 | Ring et al. |
| 4,588,693 A | 5/1986 | Strobel |
| 4,618,496 A | 10/1986 | Brasseur |
| 4,624,790 A | 11/1986 | Kamperman et al. |
| 4,676,196 A | 6/1987 | Lojek et al. |
| 4,704,818 A | 11/1987 | Cameron |
| 4,788,146 A | 11/1988 | Ring et al. |
| 4,798,723 A | 1/1989 | Dart et al. |
| 4,827,871 A | 5/1989 | Morrison |
| 4,936,910 A | 6/1990 | Dadgar et al. |
| 4,941,282 A | 7/1990 | Milstein |
| 4,971,702 A | 11/1990 | Renk |
| 4,999,202 A | 3/1991 | Cronje et al. |
| 5,049,002 A | 9/1991 | Cole |
| 5,049,265 A | 9/1991 | Boyd et al. |
| 5,060,598 A | 10/1991 | Richards |
| 5,108,614 A | 4/1992 | Ross et al. |
| 5,118,504 A | 6/1992 | Clement et al. |
| 5,178,769 A | 1/1993 | Simpson et al. |
| 5,181,802 A | 1/1993 | Thengs et al. |
| 5,187,200 A | 2/1993 | Rainer |
| 5,242,582 A | 9/1993 | Marioni |
| 5,271,987 A | 12/1993 | Iskra |
| 5,290,554 A | 3/1994 | Tolpa et al. |
| 5,296,293 A * | 3/1994 | Jobst .................... 428/403 |
| 5,346,514 A | 9/1994 | Molnar et al. |
| 5,360,117 A | 11/1994 | Tolpa et al. |
| 5,360,608 A | 11/1994 | Harman et al. |
| 5,373,025 A | 12/1994 | Gay |
| 5,378,460 A | 1/1995 | Zuckerman et al. |
| 5,389,257 A | 2/1995 | Todd et al. |
| 5,403,584 A | 4/1995 | Crawford et al. |
| 5,418,165 A | 5/1995 | McBeath |
| 5,454,191 A | 10/1995 | Mayeda et al. |
| 5,476,523 A | 12/1995 | Hiraoka |
| 5,476,591 A | 12/1995 | Green |
| 5,478,463 A | 12/1995 | Brownawell et al. |
| 5,527,526 A | 6/1996 | Crawford |
| 5,533,300 A | 7/1996 | Kesler |
| 5,543,300 A | 8/1996 | Inglot et al. |
| 5,549,889 A | 8/1996 | Zuckerman et al. |
| 5,580,192 A | 12/1996 | Ogawa et al. |
| 5,584,140 A | 12/1996 | Byrne |
| 5,597,489 A | 1/1997 | Schneider et al. |
| 5,602,071 A | 2/1997 | Summers et al. |
| 5,608,989 A | 3/1997 | Behrens |
| 5,635,029 A | 6/1997 | Levesque et al. |
| 5,688,259 A | 11/1997 | Osborn, III et al. |
| 5,690,827 A | 11/1997 | Simmering et al. |
| 5,693,220 A | 12/1997 | Sceusa |
| 5,704,989 A | 1/1998 | Page |
| 5,707,527 A | 1/1998 | Knutson et al. |
| 5,718,697 A | 2/1998 | Chauvette et al. |
| 5,747,050 A | 5/1998 | Tolpa et al. |
| 5,759,225 A | 6/1998 | Tanoshima |
| 5,797,894 A | 8/1998 | Cadieux et al. |
| 5,807,484 A | 9/1998 | Couture et al. |
| 5,814,233 A | 9/1998 | Starkey et al. |
| 5,829,193 A | 11/1998 | Otake et al. |
| 5,843,415 A | 12/1998 | Klar |
| 5,853,460 A | 12/1998 | Alcordo |
| 5,853,706 A | 12/1998 | Klar |
| 5,895,380 A | 4/1999 | Turi et al. |
| 5,934,011 A | 8/1999 | Ishioka et al. |
| 5,942,478 A | 8/1999 | Lopes |
| 5,945,446 A | 8/1999 | Laub |
| 5,980,748 A | 11/1999 | Auger et al. |
| 5,997,812 A | 12/1999 | Burnham et al. |
| 6,012,251 A | 1/2000 | Siegert |
| 6,027,639 A | 2/2000 | Lenhart, Jr. et al. |
| 6,030,533 A | 2/2000 | Karamanev et al. |
| 6,036,851 A | 3/2000 | Simmering et al. |
| 6,040,032 A | 3/2000 | Israel et al. |
| 6,042,743 A | 3/2000 | Clemenson |
| 6,048,131 A | 4/2000 | Laak |
| 6,062,220 A | 5/2000 | Whitaker et al. |
| 6,062,229 A | 5/2000 | Kandratavich et al. |
| 6,074,988 A | 6/2000 | King et al. |
| 6,096,266 A | 8/2000 | Duroselle |
| 6,100,081 A | 8/2000 | Buelna |
| 6,100,382 A | 8/2000 | Wolfe et al. |
| 6,123,036 A | 9/2000 | Decker |
| 6,132,599 A | 10/2000 | Chaffee |
| 6,187,183 B1 | 2/2001 | Weaver et al. |
| 6,190,548 B1 | 2/2001 | Frick |
| 6,197,081 B1 | 3/2001 | Schmidt |
| 6,200,469 B1 | 3/2001 | Wallace |
| 6,205,708 B1 | 3/2001 | Gatliff |
| 6,217,780 B1 | 4/2001 | Denkewicz, Jr. et al. |
| 6,242,230 B1 | 6/2001 | Batich et al. |
| 6,255,117 B1 | 7/2001 | Johnson |
| 6,264,841 B1 | 7/2001 | Tudor |
| 6,267,962 B1 | 7/2001 | Hart et al. |
| 6,271,020 B1 | 8/2001 | Coleman |
| 6,276,300 B1 | 8/2001 | Lewis, II et al. |
| 6,293,045 B1 | 9/2001 | Morgan |
| 6,319,405 B1 | 11/2001 | Roy et al. |
| 6,322,699 B1 | 11/2001 | Fernandez |
| 6,336,291 B1 | 1/2002 | Skuba |
| 6,337,025 B1 | 1/2002 | Clemenson |
| 6,337,203 B1 | 1/2002 | Beaulieu |
| 6,352,644 B1 | 3/2002 | Hawthorne et al. |
| 6,365,214 B1 | 4/2002 | Kirk |
| 6,365,384 B1 | 4/2002 | Iijima |
| 6,372,128 B1 | 4/2002 | Belhumeur |
| 6,378,244 B1 | 4/2002 | Iwata et al. |
| 6,403,366 B1 | 6/2002 | Kim |
| 6,406,627 B1 | 6/2002 | Wallace |
| 6,406,690 B1 | 6/2002 | Peleg et al. |
| 6,620,321 B2 | 9/2003 | Festa et al. |
| 6,638,959 B2 | 10/2003 | Howarth et al. |
| 6,749,748 B1 | 6/2004 | Macpherson et al. |
| 7,497,947 B2 | 3/2009 | Knighton et al. |
| 2001/0007065 A1 | 7/2001 | Blanchard et al. |
| 2001/0016721 A1 | 8/2001 | Salerno et al. |
| 2001/0025162 A1 | 9/2001 | Roe et al. |
| 2001/0027304 A1 | 10/2001 | Mayer |
| 2002/0134728 A1 | 9/2002 | Festa et al. |
| 2002/0139742 A1 | 10/2002 | Svirklys et al. |
| 2004/0031193 A1 | 2/2004 | Anderson |
| 2004/0112811 A1 | 6/2004 | Lindemulder |
| 2006/0032123 A1 | 2/2006 | Knighton et al. |
| 2006/0032124 A1 | 2/2006 | Knighton et al. |
| 2006/0231451 A1 | 10/2006 | Takeda et al. |
| 2009/0152185 A1 | 6/2009 | Knighton et al. |

FOREIGN PATENT DOCUMENTS

| | | |
|---|---|---|
| GB | 2 134 793 A | 8/1984 |
| JP | 8-1188 | 1/1996 |
| JP | 11-56096 | 3/1999 |
| JP | 2001-62478 | 3/2001 |
| JP | 2002-360060 | 12/2002 |
| WO | WO 97/07883 | 3/1997 |
| WO | WO 2004/060049 A1 | 7/2004 |
| WO | WO 2007/077459 A2 | 7/2007 |

OTHER PUBLICATIONS

Azegami et al., Effect of Iron Limitation on "*Pseudomonas plantarii*" Growth and Tropolone and Protein Production, *AEM*, 54(3):844-847 (Mar. 1988).

Banerjee et al., "Antibiotic Activity of Bryophytes[1]", The Bryologist, 82(2):141-153 (1979).

Borel et al., "Dicranin, an Antimicrobial and 15-Lipoxygenase Inhibitor From the Moss Dicranum scoparium", Journal of Natural Products, 56(7):1071-1077 (Jul. 1993).

Børsheim et al., "Preservation of Fish by Embedment in Sphagnum Moss, Peat or Holocellulose: Experimental Proof of the Oxopolysaccharidic Nature of the Preservative Substance and of its Antimicrobial and Tanning Action", ScienceDirect-Innovative Food Science & Emerging Technologies, 17 pages (Mar. 2001).

Diouf et al., Influence of Tropolone on Poria placenta Wood Degradation, AEM, 68(9):4377-4382 (Sep. 2002), HTTP://aem.asm.org/cgi/content/full/68/9/4377.

International Search Report for PCT Application No. PCT/US2005/012915 (12 pages), (2005).

"Iron Chelator Prevents Bacterial Biofilm Formation", HTTP://PUBS.ACS.ORG/CEN, C & EN, Jun. 3, 2002, p. 31.

Jones et al., "A Preliminary Study of Antimicrobial Activity in Some Malaysian Mosses (Bryophytina)", Malays. Appl. Biol., 12(1):5-13 (1983).

Latiff et al., "The Effect of Moss Extracts on the Growth of Three Species of Bacteria", Malays. Appl. Biol., 18(1):77-84 (1989).

Martins et al., "Cadmium(II) and Zinc(II) Adsorption by the Aquatic Moss Fontinalis antipyretica: Effect of Temperature pH and Water Hardness," Water Research, 38:693-699 (2004).

McCleary et al., "Mosses and Antibiosis", pp. 309-314 (date unknown).

Painter et al., "The Cation-Exchanger of Sphagnum Mosses: an Unusual Form of Holocellulose*", Carbohydrate Research, 66:C1-C3 (1978).

Podterob et al., "A History of the Medicinal Use of Plants of the Genus Sphagnum," Pharmaceutical Chemistry Journal, 36(4):192-194 (2002).

"Scientists Find Sphagnum Useful in Preserving Fish", Sichuan Animal & Veterinary Sciences, No. 9, 2001 (vol. 28, Sum 127, p. 56) (1 page).

Smidsrød et al., "Contribution of Carbohydrates to the Catio-Exchange Selectivity of Aquatic Humus From Peat-Bog Water", Carbohydrate Research, 127:267-281 (1984).

Translation of the Jun. 6, 2008 First Office Action in Chinese Application No. 200580011538.1, filed Oct. 12, 2006 (7 pages).

Van Hoof et al., Antimicrobial and Antiviral Screening of Byryophyta, pp. 223-229 (date unknown).

Verhoeven et al., "The Ecological Significance of Organochemical Compounds in Sphagnum," Acta Bot. Neerl., 46(2):117-130 (Jun. 1997).

Abstract for WO 2004/060049 A1 (1 page).

* cited by examiner

METHODS OF TREATING WATER USING DEVICES FOR WATER TREATMENT

This application is a divisional of U.S. Ser. No. 11/106,049, filed Apr. 14, 2005, now U.S. Pat. No. 7,497,947 B2, which claims the benefit of provisional application Ser. No. 60/562,196, filed Apr. 14, 2004, the contents of each of which are hereby incorporated herein by reference.

FIELD OF THE INVENTION

This invention relates to devices for water treatment, and in particular relates to devices comprising *sphagnum* moss.

BACKGROUND OF THE INVENTION

There are many types of water treatment systems, such as filtration and cleaning systems for swimming pools and aquariums. Many of these systems filter the water to remove suspended matter and reduce the cloudy appearance of the water. Preventing bacterial growth in water and removing contaminants from water are significant industrial, as well as household, problems. For example, industrial effluent should be cleaned to remove toxic compounds as well as to remove bacteria before it is dumped into lakes and rivers. Containers of water such as swimming pools, hot tubs, aquariums and the like must be kept clean to prevent the water from becoming cloudy and/or the container walls from becoming slimy. The water may be treated by active means such as a filter to remove particles and bacteria, and it may also be treated by passive means whereby a biocide is placed in a container and floated in the water.

It is common to use chemical means to keep the water clean and reduce growth of bacteria and other microorganisms. Ultraviolet light, chlorination, bromination, treatment with ions of copper and silver as well as treatment with ozone can be used to treat and/or disinfect water. These are typical biocides, that is, substances or energies that destroy living organisms. Of course care must be taken with all these methods because of the possible toxicity or damage to the user. Chemicals require careful handling to avoid environmental contamination as well as contact with the user.

"Sphagnum moss" is a generic expression that designates a range of botanical species that co-exist in a sphagnous bog. It should be noted that "peat moss" refers generally to a decomposed or composted *sphagnum* moss. Sphagnum moss is commonly harvested for use in various products. The petals, and not the stems, of the moss preferably may be harvested. Typically large pieces of plant material (roots, twigs, etc.) are removed and the moss may be processed further after harvesting by forming an aqueous slurry to extract very fine particles. Water is removed from the slurry and the moss is dried. The moss may be compressed prior to packaging or shipment. Various additives may be used to alter the absorption characteristics or mechanical properties of the moss. Because *sphagnum* moss is readily available and relatively inexpensive, it has been used in a variety of products, primarily for the absorption of fluids.

There is substantial need in the art for products that inhibit the growth of microorganisms such as bacteria, yeast, and algae. It would be desirable to have a means to maintain the clarity of water in a swimming pool, whirlpool bath, aquarium, and the like, for long periods of time, without shutting a system down for cleaning. The most desirable system would require very little maintenance and would be relatively inexpensive.

SUMMARY OF THE INVENTION

The invention provides a device for use in water comprising: (i) a carrier having an interior cavity and one or more openings allowing ingress to and egress from the interior cavity; and (ii) a moss contained within the interior cavity, wherein the carrier completely encloses the moss.

The invention provides a method of inhibiting microorganism growth comprising placing in water susceptible to bacterial growth a device for inhibiting microorganism growth in water, the device comprising: (i) a carrier having an interior cavity and one or more openings allowing ingress to and egress from the interior cavity; and (ii) a moss contained within the interior cavity, wherein the carrier completely encloses the moss, and wherein the device comprises an amount of the moss effective to inhibit microorganism growth in the water.

The invention provides a kit comprising sterilized, non-decomposed moss and a device for use in water comprising a carrier having an interior cavity and one or more openings allowing ingress to and egress from the interior cavity, wherein the interior cavity can completely enclose the moss.

The invention provides a method of inhibiting microorganism growth comprising placing in water susceptible to microorganism growth a device for inhibiting microorganism growth in water, the device comprising: (i) a carrier having an interior cavity and one or more openings allowing ingress to and egress from the interior cavity; and (ii) a moss contained within the interior cavity, wherein the carrier completely encloses the moss, wherein the device comprises an amount of the moss effective to inhibit microorganism growth in the water, and periodically shocking the water with an appropriate chemical agent.

The invention provides a method of treating water comprising placing in water a device comprising: (i) a carrier having an interior cavity and one or more openings allowing ingress to and egress from the interior cavity; and (ii) a moss contained within the interior cavity, wherein the carrier completely encloses the moss, and wherein the device comprises an amount of the moss effective to remove cations other than hydrogen ions from the water.

It is to be understood that both the foregoing general description and the following detailed description are exemplary and explanatory and are intended to provide further explanation of the invention as claimed.

DETAILED DESCRIPTION OF THE PREFERRED EMBODIMENTS

We have discovered species of *sphagnum* moss that can be used to treat water such as in a swimming pool, spa, aquarium, whirlpool, and the like. It is believed that particular species of moss are particularly effective at inhibiting and/or preventing the growth of bacteria and other microorganisms.

In this invention, "bacteriostatic" refers to a material that inhibits the growth of bacteria. In common lexicography, the term "antibacterial" generally refers to a bacterial growth inhibitor. Both terms should be distinguished from "bactericidal" which refers to materials that kill bacteria upon contact.

In this invention, "water treatment" refers to a process by which water is kept clean, clear, and pleasant smelling in swimming pools, aquariums, spas, and the like. Spas are also known as whirlpools or hot tubs. When the water is agitated, less foaming is observed. The moss is believed to inhibit growth of bacteria and other microorganisms and it also may absorb compounds and substances that decrease water clarity.

In this invention, *sphagnum papillosum* (*S. papillosum*) and/or *sphagnum cristatum* (*S. cristatum*) can be used in water treatment devices. In preferred embodiments, the moss is enclosed or encapsulated in a mesh material that prevents the moss from disintegrating in an aqueous environment. Thus the moss can be held in a desired place in a pool, hot tub, whirlpool bath, and the like. Preferred mesh materials include those comprising polymers such as nylon or polypropylene, with mesh sizes ranging from about 0.1 to 1 mm. Polymers are generally preferred because they are inexpensive and may be resistant to degradation.

Suitable for use in this invention are *S. papillosum*, which can be harvested from bogs in northern Minnesota, U.S.A., and *S. cristatum*, which is commercially available as a compressed bale from Sutton's Moss of Dobson, Westland, New Zealand. These species of moss can be used by themselves or together in the devices and systems of this invention. Typically and preferably the moss is cleaned to remove small particles, such as dirt, and larger debris, such as roots and leaves. Commercially available moss may be fumigated before it is packaged by a manufacturer in order to destroy seeds.

In a preferred embodiment, the moss is cut by mechanical means into a desired size and shape. The moss preferably is then sterilized by autoclaving, exposure to ethylene oxide, or by other means known to one of skill in the art. Sterilization destroys living organisms in the moss and thus avoids any problems of undesirable or foreign bacteria being introduced into the environment where a device of this invention is used. The moss is then ready for use in a water treatment system or other applications.

We have found that a convenient, easy, effective, and inexpensive way of treating water is to place a portion of *S. papillosum* or *S. cristatum* in a floatation device that permits water to flow around and through the moss. Another way to use it is to encapsulate it in mesh and weight the mesh so that the moss will remain in the water. Any suitable means that will maintain contact of the moss with water is suitable for use. This device is then placed in the swimming pool, whirlpool, hot tub, etc., where it can come into contact with the water. We have found that treatment is remarkably effective in preventing growth of microorganisms and in keeping the water clean, clear and free of odor and foam. This is all the more remarkable because this is a passive system when compared to a filtration system which forces water through the moss. Of course it is to be understood that active filtration could be done with the device of this invention to treat the water.

When used in swimming pools, hot tubs, and the like, the water treatment devices described herein are preferably used in conjunction with materials that kill microorganisms. This is because these environments may have large loads of microorganisms, particularly bacteria, introduced at various times. Accordingly, standard practice is to filter the water, flush water lines, and test the water as necessary. The pH can be adjusted by using commercially available solutions. The water treatment devices of this invention are most desirably used in conjunction with an oxidizer, such as potassium monopersulfate, referred to as "chlorine free shock". Potassium monopersulfate is known to increase the efficiency of chlorine purification products, but we have found that it is also particularly effective when used with the *sphagnum* moss devices described above.

The *sphagnum* moss of this invention can be used in any composition, material, device, or method where the inhibition of bacteria is desirable. Uses include the inhibition of microorganism growth, the reduction and/or prevention of odors, water treatment, and control of mold and fungal growth; and control of fermentation. Such devices and materials include absorbent products, such as diaper liners, feminine hygiene products, bandages, and wound dressings. In such products, the moss can be enclosed between membranes of differing liquid transmission characteristics. That is, for example, one membrane may be permeable to fluid and another membrane may be permeable to vapor. The moss can be incorporated into polymers and used as face masks. The moss can be encapsulated in membranes and used in food preservation products such as packaging wraps and liners to absorb liquid and odors. The moss can be used in water treatment products to keep water clean in storage tanks, aquariums, swimming pools, whirlpool baths, spas, and the like, as well as in water filtration devices. The moss can be used for waste water and sewage treatment. The moss can be shaped into, for example, discs or pellets, and used to absorb water from grain and other food products. The moss also can be used for fermentation control (such as in liquids or grains). The moss can be used for the control of fungal or bacterial diseases in lawns and gardens. The moss can be used for mold control products such as in storage containers or ductwork linings.

The invention provides a device for use in water comprising: (i) a carrier having an interior cavity and one or more openings allowing ingress to and egress from the interior cavity; and (ii) a moss contained within the interior cavity, wherein the carrier completely encloses the moss. The carrier can comprise a float. The carrier can comprise a float and a cylindrical portion beneath the float, the cylindrical portion having an interior cavity and one or more openings allowing ingress to and egress from the interior cavity. The moss can be enclosed within a mesh bag. The carrier can comprise one or more weights.

The moss can be non-decomposed moss. The moss can be *sphagnum* moss. The moss can be selected from the group consisting of *sphagnum papillosum, sphagnum cristatum*, and mixtures thereof. The moss can be compressed and can be in the form of strips. The moss can be sterilized by autoclaving, sterilized by chemical treatment, or sterilized by treatment with ethylene oxide. The moss can be washed with an acidic solution, especially a solution of acetic acid. The moss can be washed with an acidic solution and then washed with a salt solution.

The invention provides a method of inhibiting microorganism growth comprising placing in water susceptible to microorganism growth a device for inhibiting microorganism growth in water, the device comprising: (i) a carrier having an interior cavity and one or more openings allowing ingress to and egress from the interior cavity; and (ii) a moss contained within the interior cavity, wherein the carrier completely encloses the moss, and wherein the device comprises an amount of the moss effective to inhibit microorganism growth in the water. The water can be in a spa, pool, or aquarium. The water can be pumped through the device.

The invention provides a kit comprising sterilized, non-decomposed moss and a device for use in water comprising a carrier having an interior cavity and one or more openings allowing ingress to and egress from the interior cavity, wherein the interior cavity can completely enclose the moss. The kit can comprise one or more pH test strips and/or potassium monopersulfate.

The invention provides a method of inhibiting microorganism growth comprising placing in water susceptible to microorganism growth a device for inhibiting microorganism growth in water, the device comprising: (i) a carrier having an interior cavity and one or more openings allowing ingress to and egress from the interior cavity; and (ii) a moss contained within the interior cavity, wherein the carrier completely encloses the moss, wherein the device comprises an amount of the moss effective to inhibit microorganism growth in the water, and periodically shocking the water with an appropriate chemical agent. The chemical agent can be potassium monopersulfate.

The invention provides a method of treating water comprising placing in water a device comprising: (i) a carrier having an interior cavity and one or more openings allowing ingress to and egress from the interior cavity; and (ii) a moss contained within the interior cavity, wherein the carrier completely encloses the moss, and wherein the device comprises an amount of the moss effective to remove cations other than hydrogen ions from the water. The cations can be calcium or iron ions, and substantially all of the calcium or iron ions can be removed from the water. The moss can be compressed and can be in the form of strips. The moss can be sterilized by autoclaving, sterilized by chemical treatment, or sterilized by treatment with ethylene oxide. The moss can be washed with an acidic solution, especially a solution of acetic acid. The moss can be washed with an acidic solution and then washed with a salt solution. The water can be in a spa, pool, or aquarium.

Figure 1A:
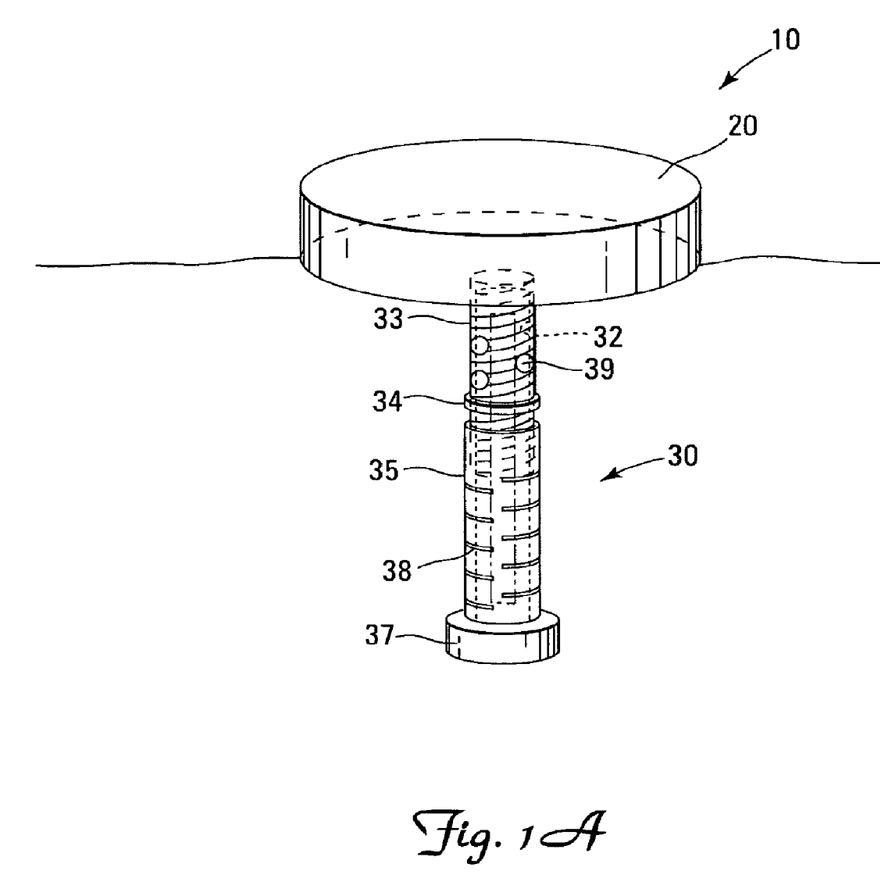
FIG. 1A illustrates a perspective view of one embodiment of the device of this invention.
Figure 1B:
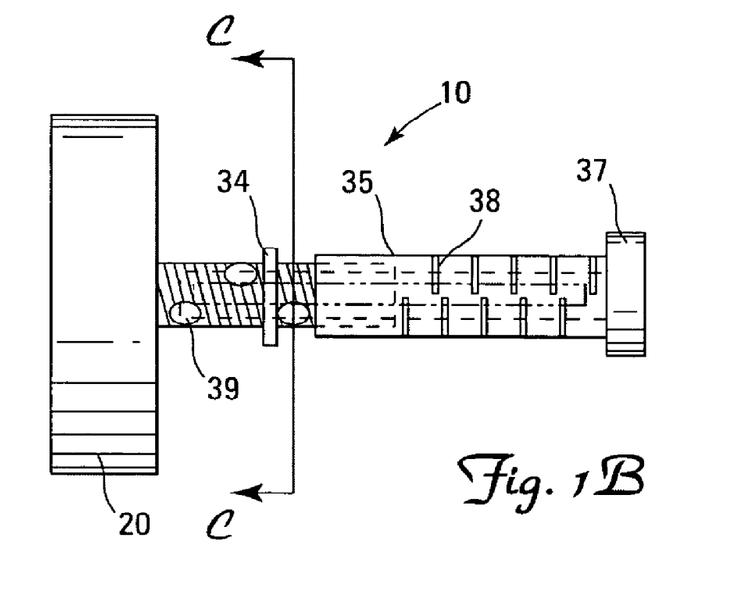
FIG. 1B illustrates a side view.
Figure 1C:
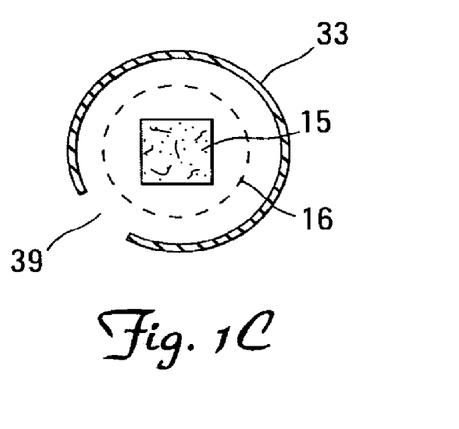
FIG. 1C illustrates a cross-sectional view along line C-C of FIG. 1B.

FIGS. 1A to 1C illustrate a suitable device of this invention. FIG. 1A shows device 10 floating in water and FIGS. 1B and 1C shows side and cross sectional views, respectively. Device 10 is adapted to receive a segment of compressed *sphagnum* moss 15 that has been cut into a desired dimension. The moss is shown in phantom in FIGS. 1A and 1B. A convenient dimension for the moss used in device 10 is about 6×¼×¼ inches (15.2×0.63×0.63 cm). A piece of moss this size weighs about 5 grams. Moss 15 is enclosed in nylon mesh 16, sized to permit the compressed moss to expand. The mesh size is such that it will retain even small particles of moss and prevent it from breaking apart and floating away.

Device 10 comprises a plastic material that is impact resistant, does not dissolve in water, and can be shaped into a desired shape. Device 10 is commercially available as a "floater" from MP Industries of Huntington Beach, Calif. It should be noted that floaters of this type are commonly used with pellets or discs of pool cleaning agents, such as those containing chlorine. Device 10 has been adapted for use with *sphagnum* moss by adding holes to facilitate passage of water into the device.

Device 10 comprises float portion 20 and flow through portion 30. Float portion 20 is cylindrical, and may be any desired dimension, though typically it is larger in diameter than flow-through portion 30. A useful dimension for the float portion is about 5 inches (12.7 cm) in diameter.

Flow-through portion 30 is a two-part elongated cylinder having core or hollow center 32. First part 33 is attached to floatation portion 20 and is provided with screw threads onto which second part 35 affixes. In this way the length of the flow-through portion can be changed. Second part 35 is fixed in position by means of adjustable collar 34. Second part 35 also has removable cap 37, which is weighted so that device 10 floats in the water as illustrated in FIG. 1.

Slots 38 and holes 39 permit water to flow through the cylinder. The slots and holes may be any desired dimension and can be positioned as desired. A useful length of the flow through portion is about 7 inches (17.8 cm). Cap 37 is removable so that the desired size of the *sphagnum* moss can be inserted into portion 30. Once exposed to water, the compressed moss expands. The density of expanded moss is such that water can permeate it. Device 10 is sufficient to treat up to about 500 gallons of water (for example, in a whirlpool or spa) for up to 30 days.

Figure 2A:
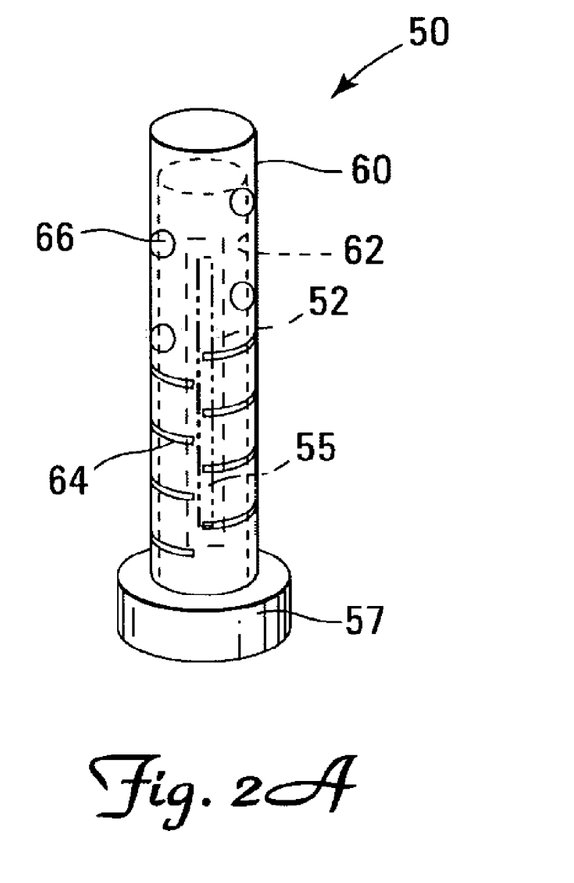
FIG. 2A illustrates a perspective view of another embodiment of the device of this invention and FIG. 2B shows a side view of the moss used within the device shown in FIG. 2A.
Figure 2B:
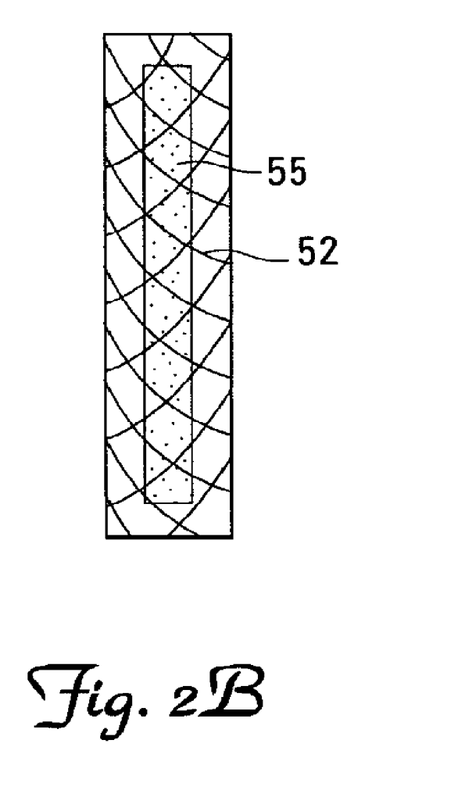

FIG. 2A illustrates device 50 floating in water. Device 50 comprises cylindrical portion 60 having core or hollow center 62. Slots 64 and holes 66 permit water to enter the hollow center. Moss 55, shown in phantom in FIG. 2A, is encapsulated by mesh 52, as most clearly shown in FIG. 2B. The moss expands when in contact with the water, filling hollow center 62. Cylindrical portion 60 is shown sealed at one end, with removable cap 57 at the other end. Cap 57 may be weighted so that the maximum length of device 60 stays in contact with the water.

Figure 3:
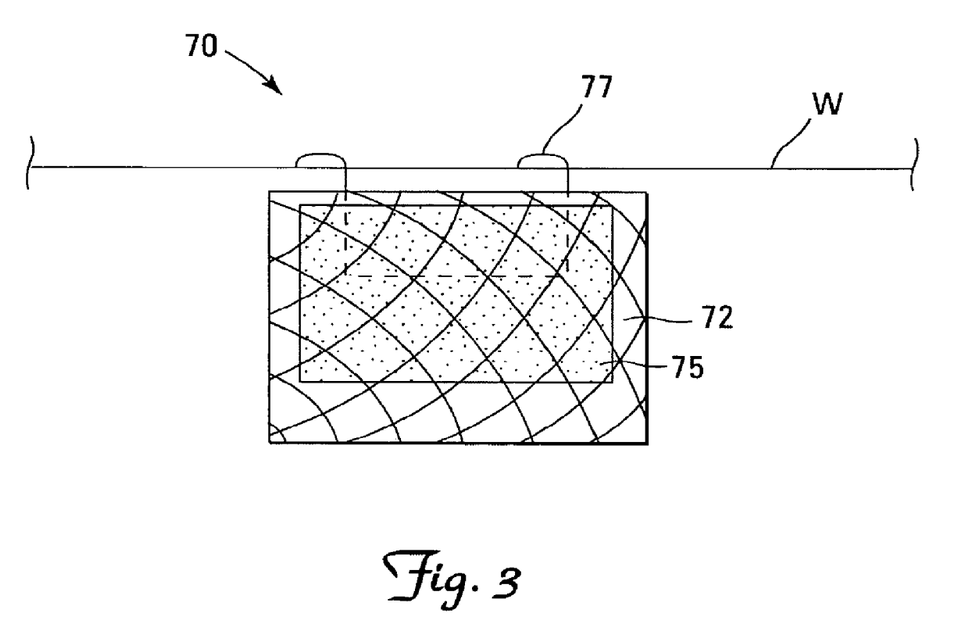
FIG. 3 illustrates a perspective view of another embodiment of the device of this invention.

FIG. 3 shows device 70 attached to wall W of a swimming pool, aquarium, hot tub, or the like. Moss 75 is encapsulated by mesh 72 and the mesh is affixed to bracket 77. The mesh is of a sufficient size that particles or fragments of moss will stay within the mesh. The bracket hangs from the wall and the device can remain fixed at this location. Alternatively, device 70 could lie on the bottom of the pool or tub. It could be affixed there or could be held down by a weight. It could also be placed in-line with a filter.

EXAMPLES

Example 1

*S. papillosum* moss, harvested from northern Minnesota, and was prepared for bacterial inhibition testing. The moss species was validated by the University of Minnesota and again upon receipt.

All samples were placed in plastic bags. All raw moss was stored at 4° C. until processed by lab personnel. All pre-dried outside moss samples were stored at room temperature until processed.

The following equipment was used:
a) Blender, 1.25 L capacity (commercially available as Osterizer® from Oster)
b) Distilled Water (available from Premium Water, Inc.)
c) Tissue Sieve, 1 cup capacity (commercially available as Cellector® E-C Apparatus Corp.)
d) 1 L Glass Beaker (commercially available as Pyrex®)
e) Sterile Polystyrene Petri Dishes 100×15 mm (commercially available from Falcon)
f) Sterile Polystyrene Petri Dishes 150×15 mm (commercially available from VWR)
g) Autoclave (commercially available from Market Forge)
h) Metal Lab Scoop (16.5 cm)/commercially available as Adison Tissue Forceps from VWR)
i) Laminar Flow Hood (commercially available from Baker)

Procedure:
1) Raw moss was taken out of the bag by hand and picked clean of any visible, roots, leafs and debris and placed in the blender. The blender was then filled with moss until it reached approximately the 1 L mark.

2) The blender was then filled with 1 L of distilled water and shaken manually with the lid on for 30 seconds and drained to remove any remaining dirt and debris. The process was repeated 2 more times to thoroughly wash the moss.
3) The blender was then filled with distilled water again and the moss was blended using the pulse mode on settings 4 and 5 for 30 seconds each until the moss was homogeneous throughout the sample.
4) The blender was then drained of water. Any remaining water was then squeezed out by hand from the moss using the tissue sieve. The squeezed moss was then placed in a clean 1 L beaker. Steps 1 to 4 were repeated until the 1 L beaker was filled with processed moss. The beaker was then autoclaved for 20 minutes at 121° C. at 15 psi (103.4 MPa) using the liquid setting and allowed to cool at room temperature.
5) Once cooled, the moss was brought to the laminar flow hood and carefully placed in labeled, pre-weighed Petri dishes using a sterile lab scoop and forceps. Special care was taken not contaminate the moss and to pack each dish in a uniform manner. Once packed, the dishes remain uncovered for at least 72 hours until the moss was dry. The dried dishes were covered and kept in the flow hood until used.

Example 2

*S. cristatum* moss, obtained from Sutton's Moss, Canada, (harvested in New Zealand) was prepared for bacterial inhibition testing. The moss species was validated upon receipt. Handling of the moss samples was identical to that described above in Example 1.

The following equipment was used:
a) Sterile syringes, individually wrapped 30 cc or 60 cc (commercially available from Becton Dickenson)
b) Sterile syringe filters, 0.45 μm (micrometer) and 0.20 μm (commercially available as Acrodisc from Pall Gellman)
c) Adison tissue forceps (commercially available from VWR)
d) 50 cc polypropylene graduated test tubes, sterile pack (commercially available from Falcon)
e) Wax film (Parafilm®, commercially available from American National Can)
f) Laminar flow hood (commercially available from Baker Company)
g) Pipetman with sterile graduated polypropylene tips, 25 mL (commercially available from Becton Dickenson)
h) 10 M HCl and 10 M NaOH
i) pH Meter (commercially available from Beckman Omega 40)

Reagents and Solutions Preparations: (Depending on liquid used for treatment)
a) Bacto™ Tryptic Soy Broth, 30 g/L (Becton Dickenson)/ MEM-Alpha (Gibco)
b) Phosphate Buffered Saline (1×), pH 7.1 (commercially available from Gibco™)
c) HPLC Grade Water (commercially available from J. T. Baker)

Procedure
a) All liquids used for treatment were either autoclaved or filter sterilized and stored at a proper temperature prior to use in this protocol. All treatment steps were done with in the laminar flow hood using aseptic technique. Tissue forceps used were autoclaved prior to use.
b) After weighing the dried moss, the treatment liquid was pipetted into the Petri dish at a concentration of one milliliter of treatment liquid to every 50 mg dried moss. If a concentration other that 50 mg/mL was used, the process changed accordingly.
c) The Petri dish of moss was wrapped in wax film (Parafilm®) and refrigerated at 4° C. for one hour.
d) The Petri dish was removed from the refrigerator and the moss was scooped and packed into a 30 cc or 60 cc syringe using sterile tissue forceps. The plunger of the syringe was re-inserted and the liquid was squeezed into a sterile 50 mL polypropylene test tube until all possible liquid was extracted.
e) The treatment liquid was filtered through a 0.45 μm syringe filter, then a 0.2 μm syringe filter and stored at 4° C. until used.
f) Filtered samples were pH adjusted using 1.0 M HCl/NaOH and sterile filtered with a 0.2 μm syringe filter and stored again at 4° C. until used in the bacteria inhibition assay.

Example 3

This experiment determined the amount of bacterial growth in Tryptic Soy Broth (TSB) by an inhibition assay.

All *S. papillosum* and *S. cristatum* moss treatment samples used in this assay were prepared as described above. TSB was also prepared, autoclaved and stored at 4° C. prior to use.

The following equipment was used:
a) Beckman® DU-64 Spectrophotometer
b) Incubator Oven (commercially available from Boekel Instruments Model #133000)
c) 5 mL and 50 mL Polystyrene Tubes (commercially available from Falcon)
d) 10 μL and 1 mL polypropylene tips (commercially available from Pipetman)

Reagents and Solutions:
a) Bacto® Tryptic Soy Broth (TSB), 30 g/L (commercially available from Becton Dickenson)
b) *Escherichia Coli* frozen culture stock grown in TSB for a minimum of 3 log growth phases (Clinical isolate)
c) *Staphylococcus Aureus* frozen culture stock grown in TSB for a minimum of 3 log growth phases. (ATCC Strain #29213 (American Type Culture Collection of Manassas, Va.))
d) Distilled Water (commercially available from Premium Water Inc.)
e) TSB treatment sample of *S. papillosum* moss and New Zealand moss Procedure:
1) TSB nutrient broth was prepared by adding 30 g/L Bacto® Tryptic Soy Broth to distilled water. The solution was stiffed with a stir-bar until all the powder was dissolved and autoclaved at 121° C. for 20 minutes. The *S. papillosum* sample was prepared as described in B, above. One mL of the solutions, TSB or moss-treated TSB sample, was pipetted into 3 to 5 mL polystyrene test tubes.
2) Frozen aliquots of *E. coli* and *S. aureus* stored at −20° C. were allowed to thaw to room temperature. Once thawed, 100 μL of each bacterial stock was added to a 10 mL aliquot of TSB. Each tube was then capped, thoroughly mixed, labeled and placed in the incubator at 37° C.
3) Ten μL of bacteria stock was pipetted into the one mL solutions and the tubes were incubated at 37° C. for the desired time. One tube in each sample and time point did not receive bacteria in order to serve as the blank.
4) The solutions were removed from the 37° C. oven at the assigned time points and placed in an ice bath. Samples were then immediately read on the spectrophotometer at 550 nm. The absolute OD value was sample minus the blank. Inhibition was measured as percent decrease in OD value vs. the appropriate TSB control sample.

Example 4

The following data illustrate the effect of treatment of bacterial growth media (i.e., Tryptic Soy Broth) with various moss species according to the procedure in Example 3. Non-*sphagnum* species are very poor at preventing *E. coli* growth. Of the moss tested below, the most effective *sphagnum* mosses to prevent *E. coli* growth were *S. papillosum* and *S. cristatum*. "N" refers to the number of tests, "Range" presents the highest and lowest numbers obtained for these tests; and "Mean" refers to the mean value of the tests.

|  | % Inhibition of Bacterial Growth | | |
| --- | --- | --- | --- |
|  | Mean | N | Range |
| *Sphagnum* Species | | | |
| *S. papillosum* (MN) | 48 | 10 | 26-71 |
| *S. cristatum* (NZ- Sutton Moss) | 45 | 8 | 31-62 |
| *S. magellanicum* (WI - Mosser Lee) | 34 | 7 | 21-43 |
| *S. fuscum* (MN) | 20 | 1 | — |
| *S. falcatulum* (NZ) | 7 | 2 | 2-11 |
| Non-*Sphagnum* Species | | | |
| Sheet Moss (WI - Mosser Lee) | 4 | 1 | — |
| Spanish Moss (WI - Mosser Lee) | −2 | 1 | — |

Example 5

TSB was treated with *S. papillosum* and the ability of this solution to support bacterial growth was measured according to Example 3. The percent inhibition of bacterial growth for *E. coli* (clinical isolate) and *S. aureus* (ATCC Strain #29213) is reported. A TSB Control sample and moss-treated TSB solutions (MT-TSB) are reported below. The OD of a blank (B) is subtracted from the measured OD (Meas.) of the sample to obtain the reported Value.

|  | *E. coli* | | | *S. aureus* | | |
| --- | --- | --- | --- | --- | --- | --- |
| Test Material | B | Meas. | Value | B | Meas. | Value |
| TSB | 0.063 | 0.744 | 0.681 | 0.063 | 0.250 | 0.187 |
| (Control) |  | 0.726 | 0.663 |  | 0.257 | 0.194 |
| Mean |  |  | 0.672 |  |  | 0.191 |
| SD |  |  | 0.013 |  |  | 0.005 |
| MT-TSB | 0.109 | 0.662 | 0.553 | 0.109 | 0.279 | 0.170 |
| (5 mg/mL) |  | 0.714 | 0.605 |  | 0.285 | 0.176 |
| Mean |  |  | 0.579 |  |  | 0.173 |
| SD |  |  | 0.037 |  |  | 0.004 |
| % Inhibition |  |  | 13.84 |  |  | 9.19 |
| MT-TSB | 0.131 | 0.575 | 0.444 | 0.131 | 0.278 | 0.147 |
| (10 mg/mL) |  | 0.748 | 0.617 |  | 0.274 | 0.143 |
| Mean |  |  | 0.531 |  |  | 0.145 |
| SD |  |  | 0.122 |  |  | 0.003 |
| % Inhibition |  |  | 21.06 |  |  | 23.88 |
| MT-TSB | 0.173 | 0.662 | 0.489 | 0.173 | 0.276 | 0.101 |
| (25 mg/mL) |  | 0.652 | 0.479 |  | 0.284 | 0.111 |
| Mean |  |  | 0.484 |  |  | 0.107 |
| SD |  |  | 0.007 |  |  | 0.006 |
| % Inhibition |  |  | 27.98 |  |  | 43.83 |
| MT-TSB | 0.243 | 0.599 | 0.356 | 0.243 | 0.355 | 0.112 |
| (50 mg/mL) |  | 0.564 | 0.321 |  | 0.352 | 0.109 |
| Mean |  |  | 0.339 |  |  | 0.111 |
| SD |  |  | 0.025 |  |  | 0.002 |
| % Inhibition |  |  | 49.63 |  |  | 41.99 |
| MT-TSB | 0.284 | 0.388 | 0.104 | 0.284 | 0.361 | 0.077 |
| (75 mg/Ml) |  | 0.430 | 0.146 |  | 0.355 | 0.071 |
| Mean |  |  | 0.125 |  |  | 0.074 |
| SD |  |  | 0.030 |  |  | 0.004 |
| % Inhibition |  |  | 81.40 |  |  | 61.15 |
| MT-TSB | 0.274 | 0.322 | 0.048 | 0.274 | 0.322 | 0.048 |
| (100 mg/mL) |  | 0.339 | 0.065 |  | 0.310 | 0.036 |
| Mean |  |  | 0.057 |  |  | 0.042 |
| SD |  |  | 0.012 |  |  | 0.008 |
| % Inhibition |  |  | 91.59 |  |  | 77.95 |

Example 6

This example demonstrates that treatment with moss does not kill the bacteria but it does inhibit their growth. A fluorescence assay, commercially available from Molecular Probes, Eugene, Oreg., Kit No. L-7012, was used to determine the viability of bacteria. This system uses mixtures of green and red fluorescent nucleic acid stains that have differing ability to penetrate viable and non-viable bacterial cells. The green fluorescent strain, which emits at 500 nm, binds to both viable and non-viable bacteria. The red fluorescent strain, which emits at 650 nm, binds only to non-viable bacteria. Therefore, a bacterial sample containing a higher proportion of non-viable bacteria will have an altered staining ratio. The data show that for both *E. coli* and *S. aureus*, the ratio of viable to non-viable bacteria remains the same as in the control sample.

Procedure:

1. 100 µL was incubated in 10 mL of media (pH controlled TSB and S. papillosum sample, as prepared in Examples 1 and 2, respectively) for 3 hours at 37° C.
2. This mixture was centrifuged to concentrate the bacteria, which was then resuspended in 10 mL phosphate buffered saline (PBS).
3. Three mL of resuspended bacteria were added to each of three cuvettes.
4. 40 µL Styo-9 dye was mixed with 40 µL Propidium Iodide dye. Caution should be used as these compounds are believed to be carcinogens.
5. 9 µL of the mixed dye solution was added to each cuvette and stored in the dark for 15 minutes.
6. Two PBS cuvettes were prepared with no dye and two PBS cuvettes were prepared with dye to be used as blanks.
7. The solutions were mixed thoroughly. The fluorescence intensity is measured at 500 nm (with absorption at 480 nm) and at 650 nm (with absorption at 490 nm). The ratio of these two values relates to the degree of viability of the bacterial culture.

The following tables report the fluorescence intensity at two wavelengths for bacterial samples in two different media. The intensity of fluorescence at 500 nm over the intensity of the fluorescence at 650 nm creates a ratio which relates to the degree of viability of the bacterial culture. The mean of three TSB and three moss-treated TSB samples (MT-TSB) is reported below. In each case, the percent of inhibition is compared to a control sample.

| Viability Assay for *E. coli* (clinical isolate) | | | |
|---|---|---|---|
| Media | 500 nm | 650 nm | Ratio 500/650 |
| TSB | 505.117 | 5.783 | 87.3228 |
| MT-TSB of *S. papillosum* | 130.1833 | 1.5167 | 85.8352 |

| Viability Assay for *S. aureus* (ATCC Strain #29213) | | | |
|---|---|---|---|
| Media | 500 nm | 650 nm | Ratio 500/650 |
| TSB | 80.117 | 3.533 | 22.6745 |
| MT-TSB of *S. papillosum* | 45.055 | 2.0667 | 21.7984 |

The data show that there is no significant change in the ratios between TSB and the moss-treated TSB, indicating that the effect of the moss is bacteriostatic rather than bactericidal.

Example 7

Various bacteria were treated with *S. papillosum* TSB (concentration of 50 mg/mL) according to Example 3. The percent inhibition of bacterial growth is reported. Both a TSB Control sample and moss-treated TSB solutions (MT-TSB) are reported below. The "Value" is obtained by subtracting the optical density (OD) of a blank (B) from the measured OD (Meas.) of a sample.

Two studies were done and are denoted (1) and (2) below.

|  | *E. coli* (clinical isolate) | | | *S. aureus* ATCC # 29213 | | |
|---|---|---|---|---|---|---|
| Test Material (1) | B | Meas. | Value | B | Meas. | Value |
| TSB (Control) | 0.034 | 0.694 | 0.660 | 0.034 | 0.273 | 0.239 |
|  |  | 0.718 | 0.684 |  | 0.257 | 0.253 |
| Mean |  |  | 0.672 |  |  | 0.246 |
| SD |  |  | 0.017 |  |  | 0.010 |
| MT-TSB | 0.219 | 0.542 | 0.323 | 0.219 | 0.362 | 0.143 |
|  |  | 0.572 | 0.353 |  | 0376 | 0.157 |
| Mean |  |  | 0.338 |  |  | 0.150 |
| SD |  |  | 0.021 |  |  | 0.010 |
| % Inhibition |  |  | 49.7 |  |  | 39.02 |

|  | *E. coli* | | | *S. aureus* | | |
|---|---|---|---|---|---|---|
| Test Material (2) | B | Meas. | Value | B | Meas. | Value |
| TSB (Control) | 0.043 | 0.693 | 0.650 | 0.043 | 0.332 | 0.289 |
|  |  | 0.667 | 0.624 |  | 0.327 | 0.284 |
| Mean |  |  | 0.637 |  |  | 0.287 |
| SD |  |  | 0.018 |  |  | 0.004 |
| MT-TSB | 0.247 | 0.492 | 0.245 | 0.247 | 0.394 | 0.147 |
|  |  | 0.498 | 0.251 |  | 0.428 | 0.181 |
| Mean |  |  | 0.248 |  |  | 0.164 |
| SD |  |  | 0.004 |  |  | 0.024 |
| % Inhibition |  |  | 61.07 |  |  | 42.76 |

|  | *S. epidermidis* ATTC # 12228 | | | *P. aeruginosa* ATTC #10145 | | |
|---|---|---|---|---|---|---|
| Test Material(1) | B | Meas. | Value | B | Meas. | Value |
| TSB (Control) | 0.034 | 0.388 | 0.354 | 0.034 | 0.175 | 0.141 |
|  |  | 0.412 | 0.375 |  | 0.167 | 0.133 |
| Mean |  |  | 0.366 |  |  | 0.137 |
| SD |  |  | 0.017 |  |  | 0.006 |
| MT-TSB | 0.219 | 0.542 | 0.323 | 0.219 | 0.321 | 0.102 |
|  |  | 0.572 | 0.353 |  | 0.331 | 0.112 |
| Mean |  |  | 0.338 |  |  | 0.107 |
| SD |  |  | 0.021 |  |  | 0.007 |
| % Inhibition |  |  | 53.26 |  |  | 21.90 |

|  | *S. epidermidis* | | | *P. aeruginosa* | | |
|---|---|---|---|---|---|---|
| Test Material(2) | B | Meas. | Value | B | Meas. | Value |
| TSB (Control) | 0.043 | 0.349 | 0.306 | 0.043 | 0.204 | 0.161 |
|  |  | 0.327 | 0.284 |  | 0.186 | 0.143 |
| Mean |  |  | 0.295 |  |  | 0.152 |
| SD |  |  | 0.016 |  |  | 0.013 |
| MT-TSB | 0.247 | 0.428 | 0.181 | 0.247 | 0.371 | 0.124 |
|  |  | 0.444 | 0.197 |  | 0.340 | 0.093 |
| Mean |  |  | 0.189 |  |  | 0.109 |
| SD |  |  | 0.011 |  |  | 0.022 |
| % Inhibition |  |  | 35.93 |  |  | 28.62 |

|  | *C. albicans* ATTC # 10231 | | | *A. amsterodami* ATTC # 1001 | | |
|---|---|---|---|---|---|---|
| Test Material(1) | B | Meas. | Value | B | Meas. | Value |
| TSB (Control) | 0.034 | 0.068 | 0.034 | 0.034 | 0.053 | 0.019 |
|  |  | 0.069 | 0.035 |  | 0.047 | 0.013 |
| Mean |  |  | 0.035 |  |  | 0.016 |
| SD |  |  | 0.001 |  |  | 0.004 |
| MT-TSB | 0.219 | 0.249 | 0.030 | 0.219 | 0.231 | 0.012 |
|  |  | 0.245 | 0.026 |  | 0.229 | 0.010 |
| Mean |  |  | 0.028 |  |  | 0.011 |
| SD |  |  | 0.003 |  |  | 0.001 |
| % Inhibition |  |  | 18.84 |  |  | 31.25 |

|  | *C. albicans* | | | *A. amsterodami* | | |
|---|---|---|---|---|---|---|
| Test Material(2) | B | Meas. | Value | B | Meas. | Value |
| TSB (Control) | 0.043 | 0.1019 | 0.058 | 0.043 | 0.067 | 0.024 |
|  |  | 0.057 | 0.044 |  | 0.071 | 0.028 |
| Mean |  |  | 0.051 |  |  | 0.026 |
| SD |  |  | 0.010 |  |  | 0.003 |
| MT-TSB | 0.247 | 0.275 | 0.028 | 0.247 | 0.268 | 0.021 |
|  |  | 0.292 | 0.045 |  | 0.254 | 0.007 |
| Mean |  |  | 0.037 |  |  | 0.014 |
| SD |  |  | 0.012 |  |  | 0.010 |
| % Inhibition |  |  | 28.43 |  |  | 46.15 |

Example 8

Effect of Acid Treatment of the Moss

Compressed sticks of *S. cristatum* moss (obtained from Sutton's Moss, Canada (harvested in New Zealand)) were soaked in four increasing concentrations of Fe (Fe standard in concentrated HCl, 0, 0.5, 5, 50 mg/L, available from Ricca Chemicals, Arlington, Tex.) at 50 mg moss/ml in distilled water. The soaked moss was stored overnight at 4 C. The Fe solutions were extracted by syringe, filtered and measured for Fe by inductively coupled plasma atomic emission spectrometry analysis. The results showed that the moss bound significant amounts of Fe, up to 15 mg/L in the 50 mg/L sample. This experiment was run with distilled water washed moss resulting in similar results. However, it was noted that the Fe spiked samples had a low pH. Since optimal binding is at pH 4 to 6, we adjusted the pH up to between 4 and 7 on the next experiment. When the pH of the Fe samples was brought up, the Fe started to precipitate. The moss removed all of the Fe from the sample (up to 25 mg/L). It was then decided that ions bound to the moss before use could affect the cation binding tests and methods to remove the cations from the moss should be investigated.

When developing the method for acid washing Sphagnum moss (not peat moss, which is decomposed moss), two different acids were first used. One batch of moss (approx. 5 g) was constantly stirred in 3.5 L of distilled water pH adjusted to 1 with concentrated $HNO_3$. For the other batch of moss, a 2% solution of glacial acetic acid was used. The washes were stirred for 1 hour, then the supernatant was filtered off and new wash solution was put on the moss. This was repeated for a total of four acid washes. The acid washes were followed by 4 distilled water washes carried out the same way. At the end of the distilled water washes, the conductivity was similar to that of distilled water. The two acids removed similar amounts of ions; therefore acetic acid was routinely used for washing the moss thereafter.

It was decided that a metal that was soluble at neutral pH would be better suited to test binding capacity and test for improvement of binding with acid washed Sphagnum moss vs. non-washed moss. Calcium was chosen for this purpose. The moss used was the *S. cristatum* moss described earlier in this example, the acid used was a 2% solution of glacial acetic acid, and the wash was performed as described in the preceding paragraph. The first test showed the opposite of what was expected, the non-washed moss bound the most and the acid washed moss bound the least. When the pH of the samples was checked, it was discovered that the binding ability correlated with pH. The acid washed moss reduced the pH of the solutions, which affected the ion binding. To eliminate this problem, acid washed moss was washed with a high salt solution to displace the $H^+$ ions with Na. The high salt solution was 1M sodium acetate and approximately 5 g of moss was constantly stirred in 3.5 L of this sodium acetate solution for one hour, and then the wash was repeated. These two sodium acetate washes were followed by four washes with distilled water, each wash for one hour, and each was carried out the same way. The acid/salt-washed moss was tested; the pH of the extract did not drop and showed a significant improvement of binding over distilled water and non-washed moss as can be seen in the following table (concentrations of Ca are in ppm).

| Moss treatment | Starting [Ca] | Resulting Average [Ca] | Stdev | pH |
|---|---|---|---|---|
| Control | 0 | −1.08 | 0.61 | 6.02 |
| Acetic Acid, Acetate | | | | |
| Washed | 0 | −0.97 | 0.45 | 7.62 |
| No wash | 0 | −0.14 | 0.51 | 5.26 |
| Distilled water washed | 0 | 0.36 | 1.32 | 5.13 |
| washed | 100 | −1.40 | 0.25 | 6.62 |
| No wash | 100 | 11.24 | 0.00 | 4.81 |
| Distilled water washed | 100 | 16.89 | 1.17 | 4.54 |
| Control | 100 | 88.76 | 0.05 | 6.65 |
| washed | 200 | −0.33 | 0.87 | 6.17 |
| No wash | 200 | 46.47 | 5.88 | 4.82 |
| Distilled water washed | 200 | 53.55 | 4.42 | 4.61 |
| Control | 200 | 198.10 | 1.83 | 6.76 |

The pH of the extracts varied by up to 2 pH units, so it was still difficult to distinguish between the effects of acid washing and pH. Therefore a new method to test for binding of the moss was developed that would allow adjustment of pH while the moss was still in the sample solutions. This was accomplished by using multi-well plates, small stir bars and 10 mg/ml moss concentrations. After the solutions were on the moss for approximately one-half hour, the pH's of the solutions were all adjusted to within 0.25 pH units of 6.5. This allowed for the testing of acid/salt washed moss and acid only washed moss. The results are shown below. The averages shown are the averages of two samples.

| Moss treatment | Starting [Ca] | Resulting Average [Ca] | Stdev |
|---|---|---|---|
| Acetic Acid/Na acetate | | | |
| washed | 0.00 | 6.93 | 0.72 |
| Acetic Acid washed | 0.00 | 6.16 | 0.16 |
| Distilled water washed | 0.00 | 6.85 | 0.31 |
| No wash | 0.00 | 8.54 | 1.56 |
| Control | 0.00 | 8.10 | 0.31 |
| washed | 100.00 | 6.78 | 0.31 |
| Acetic Acid washed | 100.00 | 6.82 | 0.26 |
| Distilled water washed | 100.00 | 20.73 | 1.09 |
| No wash | 100.00 | 26.25 | 0.72 |
| Control | 100.00 | 92.27 | 1.56 |
| washed | 500.00 | 307.28 | 7.25 |
| Acetic Acid washed | 500.00 | 319.25 | 8.13 |
| Distilled water washed | 500.00 | 375.18 | 3.36 |
| No wash | 500.00 | 382.85 | 4.38 |
| Control | 500.00 | 454.30 | 8.91 |

With the pH's adjusted to be within 0.5 pH units of each other; the pH effect is eliminated and the significantly improved binding capacity of the acid washed mosses can be seen. The acid/salt washed moss bound slightly better than the acid only washed moss and the distilled washed slightly better than the non-washed moss, but barely enough to be significant.

Thus, the moss was shown to bind both Fe and Ca ions, and therefore is effective in water treatment because the removal of one or both of these ions is a goal of water treatment.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. A method of treating water comprising contacting water with a device for use in water, the device comprising:
   (i) a carrier having an interior cavity and one or more openings allowing ingress to and egress from the interior cavity; and
   (ii) a moss contained within the interior cavity,
   wherein the carrier completely encloses the moss, and
   wherein the carrier comprises a float and a cylindrical portion beneath the float, the cylindrical portion having an interior cavity and one or more openings allowing ingress to and egress from the interior cavity, and
   wherein the water contact the moss contained within the interior cavity and the water is treated by contact with the moss.

2. The method of claim 1, wherein the carrier comprises one or more weights.

3. The method of claim 1, wherein the moss is non-decomposed moss.

4. The method of claim 3, wherein the moss is *sphagnum* moss.

5. The method of claim 3, wherein the moss is selected from the group consisting of *sphagnum papillosum*, *sphagnum cristatum*, and mixtures thereof.

6. The method of claim 5, wherein the moss is *sphagnum papillosum*.

7. The method of claim 5, wherein the moss is *sphagnum cristatum*.

8. The method of claim 5, wherein the moss comprises *sphagnum papillosum* only.

9. The method of claim 5, wherein the moss comprises *sphagnum cristatum* only.

10. The method of claim 5, wherein the moss comprises a mixture of *sphagnum papillosum* and *sphagnum cristatum* only.

11. The method of claim 3, wherein the moss is compressed.

12. The method of claim 11, wherein the moss is in the form of strips.

13. The method of claim 3, wherein the moss has been sterilized.

14. The method of claim 3, wherein the moss has been washed with an acidic solution.

15. The method of claim 3, wherein the moss has been washed with a solution of acetic acid.

16. The method of claim 3, wherein the moss has been washed with an acidic solution and then washed with a salt solution.

17. A method of treating water comprising contacting water with a device for use in water, the device comprising:
   (i) a carrier having an interior cavity and one or more openings allowing ingress to and egress from the interior cavity; and
   (ii) a moss contained within the interior cavity,
   wherein the carrier completely encloses the moss,
   wherein the moss is non-decomposed moss, and
   wherein the moss is selected from the group consisting of *sphagnum papillosum*, *sphagnum cristatum*, and mixtures thereof, and
   wherein the water contacts the moss contained within the interior cavity and the water is treated by contact with the moss.

18. The method of claim 17, wherein the carrier comprises a float.

19. The method of claim 17, wherein the carrier comprises one or more weights.

20. The method of claim 17, wherein the moss is *sphagnum papillosum*.

21. The method of claim 17, wherein the moss is *sphagnum cristatum*.

22. The method of claim 17, wherein the moss comprises *sphagnum papillosum* only.

23. The method of claim 17, wherein the moss comprises *sphagnum cristatum* only.

24. The method of claim 17, wherein the moss comprises a mixture of *sphagnum papillosum* and *sphagnum cristatum* only.

25. The method of claim 17, wherein the moss is compressed.

26. The method of claim 25, wherein the moss is in the form of strips.

27. The method of claim 17, wherein the moss has been sterilized.

28. The method of claim 17, wherein the moss has been washed with an acidic solution.

29. The method of claim 17, wherein the moss has been washed with a solution of acetic acid.

30. The method of claim 17, wherein the moss has been washed with an acidic solution and then washed with a salt solution.

31. A method of treating water comprising contacting water with a device for use in water, the device comprising:
   (i) a carrier having an interior cavity and one or more openings allowing ingress to and egress from the interior cavity; and
   (ii) a moss contained within the interior cavity,
   wherein the carrier completely encloses the moss,
   wherein the moss is non-decomposed and compressed, and
   wherein the moss is in the form of strips, and
   wherein the water contacts the moss contained within the interior cavity and the water is treated by contact with the moss.

32. The method of claim 31, wherein the carrier comprises a float.

33. The method of claim 31, wherein the carrier comprises one or more weights.

34. The method of claim 31, wherein the moss is *sphagnum* moss.

35. The method of claim 31, wherein the moss is *sphagnum papillosum*.

36. The method of claim 31, wherein the moss is *sphagnum cristatum*.

37. The method of claim 31, wherein the moss comprises *sphagnum papillosum* only.

38. The method of claim 31, wherein the moss comprises *sphagnum cristatum* only.

39. The method of claim 31, wherein the moss comprises a mixture of *sphagnum papillosum* and *sphagnum cristatum* only.

40. The method of claim 31, wherein the moss has been sterilized.

41. The method of claim 31, wherein the moss has been washed with an acidic solution.

42. The method of claim 31, wherein the moss has been washed with a solution of acetic acid.

43. The method of claim 31, wherein the moss has been washed with an acidic solution and then washed with a salt solution.

44. A method of treating water comprising contacting water with a device for use in water, the device comprising:
   (i) a carrier having an interior cavity and one or more openings allowing ingress to and egress from the interior cavity; and (ii) a moss contained within the interior cavity,
wherein the carrier completely encloses the moss,
wherein the moss is non-decomposed moss,
wherein the moss has been sterilized, and
wherein the moss is selected from the group consisting of *sphagnum papillosum, sphagnum cristatum*, and mixtures thereof, and
wherein the water contacts the moss contained within the interior cavity and the water is treated by contact with the moss.

45. The method of claim 44, wherein the moss is *sphagnum papillosum*.

46. The method of claim 44, wherein the moss is *sphagnum cristatum*.

47. The method of claim 44, wherein the moss comprises *sphagnum papillosum* only.

48. The method of claim 44, wherein the moss comprises *sphagnum cristatum* only.

49. The method of claim 44, wherein the moss comprises a mixture of *sphagnum papillosum* and *sphagnum cristatum* only.

50. A method of treating water comprising contacting water with a device for use in water, the device comprising:
   (i) a carrier having an interior cavity and one or more openings allowing ingress to and egress from the interior cavity; and
   (ii) a moss contained within the interior cavity,
   wherein the carrier completely encloses the moss,
   wherein the moss is non-decomposed moss,
   wherein the moss has been washed with an acidic solution, and
   wherein the moss is selected from the group consisting of *sphagnum papillosum, sphagnum cristatum*, and mixtures thereof, and
   wherein the water contacts the moss contained within the interior cavity and the water is treated by contact with the moss.

51. The method of claim 50, wherein the moss is *sphagnum papillosum*.

52. The method of claim 50, wherein the moss is *sphagnum cristatum*.

53. The method of claim 50, wherein the moss comprises *sphagnum papillosum* only.

54. The method of claim 50, wherein the moss comprises *sphagnum cristatum* only.

55. The method of claim 50, wherein the moss comprises a mixture of *sphagnum papillosum* and *sphagnum cristatum* only.

56. A method of treating water comprising contacting water with a device for use in water, the device comprising:
   (i) a carrier having an interior cavity and one or more openings allowing ingress to and egress from the interior cavity; and
   (ii) a moss contained within the interior cavity,
   wherein the carrier completely encloses the moss,
   wherein the moss is non-decomposed moss, and
   wherein the moss has been washed with a solution of acetic acid, and
   wherein the water contacts the moss contained within the interior cavity and the water is treated by contact with the moss.

57. The method of claim 56, wherein the moss has been sterilized.

* * * * *